US012637649B2

(12) United States Patent
Igarashi

(10) Patent No.: US 12,637,649 B2
(45) Date of Patent: May 26, 2026

(54) SAMPLING SYSTEM AND SAMPLING METHOD

(71) Applicant: Terumo Kabushiki Kaisha, Tokyo (JP)

(72) Inventor: Masatsugu Igarashi, Kanagawa (JP)

(73) Assignee: Terumo Kabushiki Kaisha (JP)

( * ) Notice: Subject to any disclaimer, the term of this patent is extended or adjusted under 35 U.S.C. 154(b) by 292 days.

(21) Appl. No.: 18/205,184

(22) Filed: Jun. 2, 2023

(65) Prior Publication Data

US 2023/0303958 A1 Sep. 28, 2023

Related U.S. Application Data

(63) Continuation of application No. PCT/JP2022/003049, filed on Jan. 27, 2022.

(30) Foreign Application Priority Data

Feb. 2, 2021 (JP) ................................. 2021-014834

(51) Int. Cl.
*C12M 1/26* (2006.01)
*C12M 1/12* (2006.01)
(Continued)

(52) U.S. Cl.
CPC ............ *C12M 33/04* (2013.01); *C12M 33/12* (2013.01); *C12M 37/00* (2013.01); *G01N 1/2035* (2013.01);
(Continued)

(58) Field of Classification Search
CPC ...... C12M 33/04; C12M 37/00; C12M 33/00; C12M 33/12; G01N 1/2035;
(Continued)

(56) References Cited

U.S. PATENT DOCUMENTS 6,332,349 B1 * 12/2001 Poynot ............... G01N 33/0022
73/863.33
9,442,047 B2 9/2016 Biksacky
(Continued)

FOREIGN PATENT DOCUMENTS

CN 214097496 * 8/2021
JP 2016508229 A 3/2016
(Continued)

OTHER PUBLICATIONS

Written Opinion issued in corresponding International Application No. PCT/JP2022/003049 dated Apr. 5, 2022, with English translation (6 Pages).

(Continued)

*Primary Examiner* — Robert R Raevis
(74) *Attorney, Agent, or Firm* — Harness, Dickey & Pierce, P.L.C.

(57) ABSTRACT

A sampling system includes a sensor (for example, a biosensor) that is provided in a sampling channel so as to be in contact with a sample and measures concentrations of predetermined components in the sample, an introduction path that introduces a cleaning liquid to an upstream side of the sensor of the sampling channel, and an air introduction path that is connected to the introduction path and is opened to the atmosphere. The air guided from the air introduction path flows into the sampling channel via the introduction path.

19 Claims, 9 Drawing Sheets

(51) Int. Cl.
  *G01N 1/20*      (2006.01)
  *G01N 1/14*      (2006.01)
(52) U.S. Cl.
  CPC ................ *G01N 2001/1445* (2013.01); *G01N 2001/205* (2013.01)
(58) Field of Classification Search
  CPC ..... G01N 2001/1445; G01N 2001/205; C12N 5/06; C12Q 1/00
  USPC ............. 73/863.83, 1.02, 1.03, 61.43, 61.59, 73/64.56, 863, 863.01, 31, 864.22, 73/864.34, 864.81; 422/68.1
  See application file for complete search history.

(56)      References Cited

U.S. PATENT DOCUMENTS

2014/0033834 A1    2/2014  Biksacky
2014/0087413 A1    3/2014  Newbold et al.

FOREIGN PATENT DOCUMENTS

| WO | 2019180098 | * | 9/2019 |
| WO | 2020017407 | A1 | 1/2020 |
| WO | 2021/089661 | * | 5/2021 |

OTHER PUBLICATIONS

International Search Report dated Apr. 5, 2022, issued in corresponding PCT Application No. PCT/JP2022/003049 with English translation (5 pages).
Japanese Office Action issued in corresponding Japanese Application No. 2022-579492 dated Nov. 4, 2025, with English translation (7 Pages).

* cited by examiner

SAMPLING SYSTEM AND SAMPLING METHOD

CROSS-REFERENCE TO RELATED APPLICATIONS

The present application is a continuation application of the International Patent Application No. PCT/JP2022/003049 filed on Jan. 27, 2022, which designated the U.S. and claims the benefit of priority from Japanese Patent Application No. JP2021-014834 filed on Feb. 2, 2021. The entire disclosures of the above-identified applications are incorporated herein by reference.

FIELD

The present disclosure relates to a sampling system and a sampling method.

BACKGROUND

A sampling system may include a biosensor that is provided in a sampling channel so as to be in contact with a sample, and an introduction path that introduces a cleaning liquid to an upstream side of the biosensor in the sampling channel. A sampling step of circulating the sample in the sampling channel to bring the sample into contact with the biosensor, and a cleaning step of introducing the cleaning liquid from the introduction path into the sampling channel to remove the sample attached to the biosensor in order to prevent deterioration of a catalyst of the biosensor may be performed.

When the cleaning step is completed, the cleaning liquid remains on a downstream side of a connection portion in the sampling channel and the introduction path. Thereafter, when the sampling step is performed, the sample pushes away the cleaning liquid remaining in the sampling channel. However, the cleaning liquid in the introduction path remains. In such instances, there is a possibility that the cleaning liquid in the introduction path may be mixed into the sample at the connection portion during the sampling step.

An object of the present disclosure is to provide a sampling system and a sampling method capable of removing a sample attached to a biosensor and preventing a cleaning liquid from being mixed into a sample circulating through a sampling channel.

SUMMARY

In various aspects, the present disclosure provides a sampling system that includes a sampling channel configured to collect a liquid sample of a cell culture device. The sampling system may also include a biosensor that is provided in the sampling channel so as to be in contact with the sample and configured to measure concentrations of predetermined components in the sample. The sample system may also include an introduction path configured to introduce a cleaning liquid to an upstream side of the biosensor in the sampling channel and an air introduction path connected to the introduction path and opened to an atmosphere, where air guided from the air introduction path flows into the sampling channel through the introduction path.

In various aspects, the present disclosure provides a sampling method that uses a sampling system, where the sampling system includes a sampling channel that collects a liquid sample of a cell culture device, a biosensor provided in the sampling channel so as to be in contact with the sample, and an introduction path that introduces a cleaning liquid to an upstream side of the biosensor in the sampling channel. The sampling method may include a sampling step of circulating the sample from the cell culture device to the sampling channel and measuring concentrations of predetermined components in the sample by the biosensor; a cleaning step of circulating the cleaning liquid from the introduction path to the biosensor through the sampling channel after the sampling step; and an air introduction step of introducing air from the introduction path to the sampling channel, in which the sampling step is performed two or more times, and the second and subsequent sampling steps are performed after the air introduction step.

In various aspects, after a sampling step of circulating a sample from a cell culture device to a sampling channel and measuring concentrations of predetermined components in the sample by a biosensor, a cleaning step of circulating a cleaning liquid from an introduction path to the biosensor through the sampling channel can be performed. Thus, in the sampling step, the sample attached to the biosensor can be removed in the cleaning step. In addition, the air introduction step of introducing air from the introduction path to the sampling channel can be performed after the cleaning step, so that the cleaning liquid remaining in the vicinity of the connection portion with the sampling channel in the introduction path can be pushed out to the sampling channel by the air. It is therefore possible to prevent the cleaning liquid from being mixed into the sample during the sampling step.

BRIEF DESCRIPTION OF THE DRAWINGS

FIG. 1 is a schematic illustrating a sampling system according to an example embodiment of the present disclosure.

FIG. 6 is a schematic illustrating a second operation of the sampling method illustrated in FIGS. 3 and 4.

FIG. 8 is a schematic illustrating a fourth operation of the sampling method illustrated in FIGS. 3 and 4.

FIG. 9 is a schematic illustrating a fifth operation of the sampling method illustrated in FIGS. 3 and 4.

DETAILED DESCRIPTION

Figure 2:
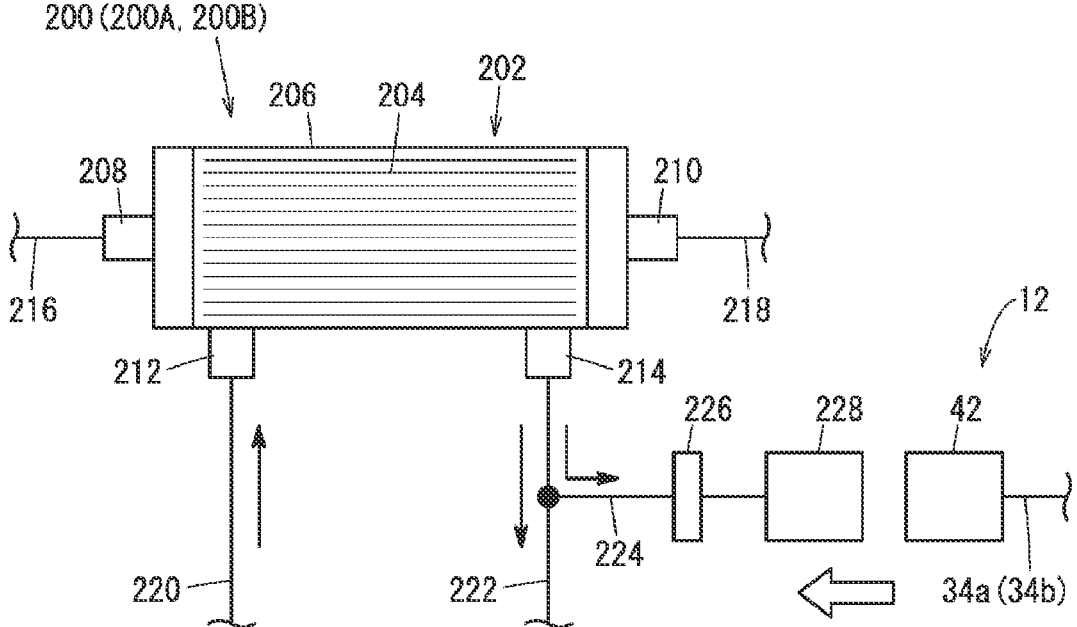
FIG. 2 is a schematic illustrating a main part of an example cell culture device according to an example embodiment of the present disclosure.

Hereinafter, an example embodiment of a sampling system and a sampling method according to the present disclosure is described with reference to the accompanying drawings.

Figure 1:
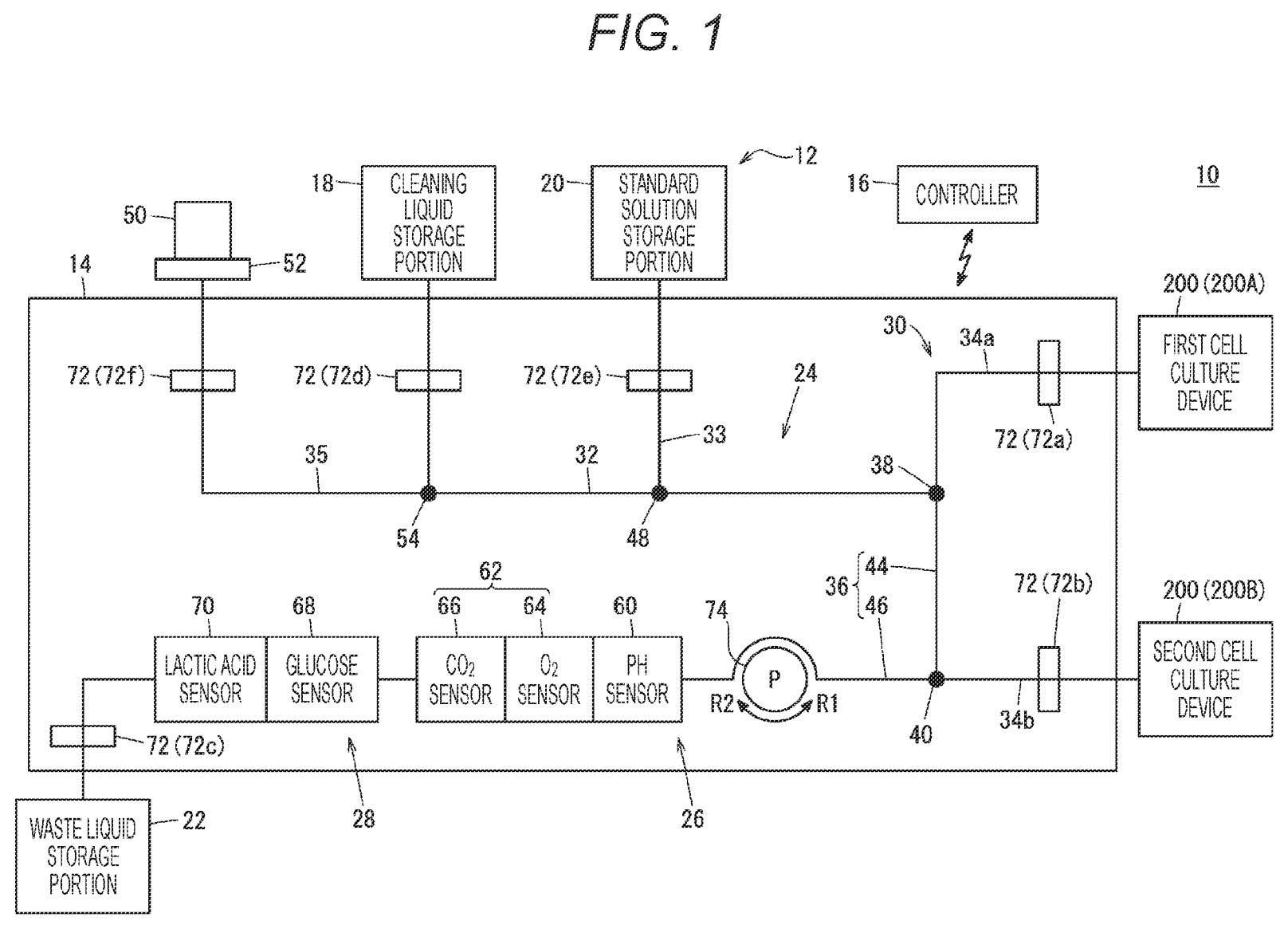

As illustrated in FIG. 1, a sampling system 10 is configured to collect liquid samples of a plurality of cell culture devices 200 and to measure concentrations of predetermined components in the samples. The sampling system 10 includes a sampling kit 12, a circuit control device 14 to which the sampling kit 12 is detachable, and a controller 16. The sampling kit 12 is a disposable product, and the circuit control device 14 is a reusable product.

In at least one example embodiment, the plurality of cell culture devices 200 may include a first cell culture device 200A and a second cell culture device 200B which are connected to the sampling kit 12. As illustrated in FIG. 2, the cell culture device 200 includes a bioreactor 202 for culturing cells. The cells to be cultured may be separated from a biological tissue. The cells may include, for example, T cells and/or stem cells (e.g., ES cells, iPS cells, mesenchymal stem cells, etc.).

The bioreactor 202 may be configured as a so-called hollow fiber bioreactor. The bioreactor 202 includes a number (for example, a plurality) of hollow fibers 204 and a cylindrical housing 206 configured to store the hollow fibers 204. A wall portion constituting the hollow fiber 204 is formed with a plurality of pores (not illustrated). Through the pores, an intracapillary (IC) region, which is a lumen of the hollow fiber 204, is communicated with an extracapillary (EC) region, which is located outside the hollow fiber 204 in the housing 206. A diameter of the pores may be set to a size that allows passage of low molecular weights (for example, water, ions, oxygen, lactate, and the like) while blocking passage of a higher molecular weights (cell or the like).

The housing 206 may be provided with an IC inlet port 208, an IC outlet port 210, an EC inlet port 212, and an EC outlet port 214. The IC inlet port 208 may be provided at one end of the housing 206. The IC inlet port 208 may be configured to introduce a liquid (for example, a solution containing cells, a medium, or the like) guided from an IC inlet flow path 216 into the IC region of the bioreactor 202. The IC outlet port 210 may be provided at the other end of the housing 206. The IC outlet port 210 directs a liquid flowing through the IC region of the bioreactor 202 to an IC outlet flow path 218.

The EC inlet port 212 and the EC outlet port 214 may be provided on an outer peripheral surface of the housing 206. The EC inlet port 212 may be configured to introduce a medium directed from an EC inlet flow path 220 into the EC region of the bioreactor 202. The EC outlet port 214 directs a medium flowing through the EC region of the bioreactor 202 to an EC outlet flow path 222. As the medium, an appropriate medium may be selected according to cells of a living body. In at least one example embodiment, a medium may be prepared, for example, by adding various amino acids, vitamins, serum, and/or the like using a balanced salt solution (BSS) as a basic solution.

A connection line 224 for guiding the culture medium circulating in the EC region to the sampling kit 12 may be connected to the EC outlet flow path 222. The connection line 224 may be provided with a sterile filter 226 and a sampling connector 228. The sterile filter 226 aseptically holds a portion of the cell culture device 200 closer to the EC outlet flow path 222 than the sterile filter 226. An introduction connector 42 of the sampling kit 12 may be detachable from the sampling connector 228.

In the present embodiment, the sampling system 10 collects, as a sample, a culture medium circulating in the EC region of the cell culture device 200. However, the sample collected by the sampling system 10 is not limited to the medium circulating in the EC region and may be, in other embodiments, a medium or another liquid circulating in the IC region.

As illustrated in FIG. 1, the sampling kit 12 includes a cleaning liquid storage portion 18, a standard solution storage portion 20, a waste liquid storage portion 22, a connection circuit 24, a first sensor 26, and a second sensor 28.

The cleaning liquid storage portion 18, the standard solution storage portion 20, and the waste liquid storage portion 22 may be formed in a bag shape using a flexible material including, for example, a soft resin, such as polyvinyl chloride or polyolefin. However, the cleaning liquid storage portion 18, the standard solution storage portion 20, and the waste liquid storage portion 22 can be appropriately changed as long as they can store liquid.

The cleaning liquid storage portion 18 stores a cleaning liquid. As the cleaning liquid, a buffer solution or physiological saline may be used. Examples of the buffer solution include phosphate buffered saline (PBS) and/or tris-buffered saline (TBS). However, the cleaning liquid is not limited to these examples.

The standard solution storage portion 20 stores a standard solution. The standard solution may include a liquid for calibrating the first sensor 26 and the second sensor 28. Specifically, the standard solution may be a liquid in which a pH value, an $O_2$ value (oxygen concentration), a $CO_2$ value (carbon dioxide concentration), a glucose value (glucose concentration), and/or a lactic acid value (lactic acid concentration) are set to prescribed values.

The waste liquid storage portion 22 stores a waste liquid (including, for example, portions of a sample, a cleaning liquid, and/or a standard solution) circulating in the connection circuit 24. The waste liquid storage portion 22 may be an empty bag in which no liquid is stored before the sampling kit 12 is used.

The connection circuit 24 may include a sampling channel 30 that collects a sample of the cell culture device 200, an introduction path 32 that guides a cleaning liquid to the sampling channel 30, a standard solution introduction path 33 that guides a standard solution to the introduction path 32, and an air introduction path 35 that guides air to the introduction path 32. The sampling channel 30 may include a first sample introduction path 34a, a second sample introduction path 34b, and a sample flow path 36.

The first sample introduction path 34a may be configured to guide the sample (i.e., culture medium) of the first cell culture device 200A to the sample flow path 36. The introduction connector 42 attached to the sampling connector 228 of the first cell culture device 200A may be provided at one end of the first sample introduction path 34a (see FIG. 2). The other end of the first sample introduction path 34a may be connected to one end of the sample flow path 36. Hereinafter, a connection portion between the first sample introduction path 34a and the sample flow path 36 is referred to as a first connection portion 38.

The second sample introduction path 34b may be configured to guide the sample (i.e., culture medium) of the second cell culture device 200B to the sample flow path 36. The introduction connector 42 attached to the sampling connector 228 of the second cell culture device 200B may be provided at one end of the second sample introduction path 34b (see FIG. 2). The other end of the second sample introduction path 34b may be connected to an intermediate portion of the sample flow path 36. Hereinafter, a connection portion between the second sample introduction path 34b and the sample flow path 36 is referred to as a second connection portion 40.

The sample flow path 36 may include an intermediate flow path 44 that connects the first connection portion 38 and the second connection portion 40 to each other, and a sensor flow path 46 that connects the second connection portion 40 and the waste liquid storage portion 22 to each other.

One end of the introduction path 32 may be connected to the cleaning liquid storage portion 18. The other end of the introduction path 32 may be connected to the first connection portion 38. One end of the standard solution introduction path 33 may be connected to the standard solution storage portion 20. The other end of the standard solution introduction path 33 may be connected to an intermediate portion of the introduction path 32. Hereinafter, a connection portion between the introduction path 32 and the standard solution introduction path 33 is referred to as a third connection portion 48.

An air port portion 50 opened to the atmosphere and a sterile filter 52 may be provided at one end of an air introduction path 35. The sterile filter 52 may be configured to hold the connection circuit 24 in a sterile state. The other end of the air introduction path 35 is connected to the introduction path 32 on an upstream side of the third connection portion 48. Hereinafter, a connection portion between the introduction path 32 and the air introduction path 35 is referred to as a fourth connection portion 54.

A first sensor 26 and a second sensor 28 may be provided in the sensor flow path 46 so as to be in contact with the sample. The first sensor 26 may be an integrally molded product and may include a pH sensor 60 and/or a gas concentration sensor 62. The pH sensor 60 measures pH in the sample. The gas concentration sensor 62 measures a gas concentration in the sample. Specifically, the gas concentration sensor 62 may include an $O_2$ sensor 64 that measures an $O_2$ concentration in the sample and/or a $CO_2$ sensor 66 that measures a $CO_2$ concentration in the sample.

The second sensor 28 may include, for example, a biosensor, such as an enzyme sensor. The second sensor 28 may be provided downstream of the first sensor 26 in the sensor flow path 46. The second sensor 28 may be an integrally molded product and may include a glucose sensor 68 that measures a glucose concentration in the sample and/or a lactic acid sensor 70 that measures a lactic acid concentration in the sample. The second sensor 28 is not limited to the enzyme sensor and may include a non-enzyme type glucose sensor. The measurement items of the second sensor 28 are not limited to glucose and lactic acid and may include glutamic acid or the like.

The circuit control device 14 may include a plurality of clamps 72 and at least one pump 74. In the at least one example embodiment, the circuit control device 14 may include, as the plurality of clamps 72, a first clamp 72a (first opening/closing portion), a second clamp 72b, a third clamp 72c, a fourth clamp 72d (second opening/closing portion), a fifth clamp 72e, and/or a sixth clamp 72f (third opening/closing portion).

The first clamp 72a may be disposed so as to face the first sample introduction path 34a in a state where the sampling kit 12 is attached to the circuit control device 14 (hereinafter, referred to as a "set state") and opens and closes an internal flow path of the first sample introduction path 34a. The second clamp 72b may be disposed so as to face the second sample introduction path 34b in the set state and may be configured to open and close an internal flow path of the second sample introduction path 34b. The third clamp 72c may be disposed so as to face a portion of the sensor flow path 46 between the second sensor 28 and the waste liquid storage portion 22 in the set state and may be configured to open and close an internal flow path of the portion of the sensor flow path 46. The fourth clamp 72d may be disposed so as to face a portion of the introduction path 32 on the upstream side of the third connection portion 48 in the set state and may be configured to open and close an internal flow path of the portion of the introduction path 32. The fifth clamp 72e may be disposed so as to face the standard solution introduction path 33 in the set state and may be configured to open and close an internal flow path of the standard solution introduction path 33. The sixth clamp 72f may be disposed so as to face the air introduction path 35 in the set state and may be configured to open and close an internal flow path of the air introduction path 35.

The pump 74 rotates so as to strip off a wall portion constituting a flow path (i.e., tube) of the connection circuit 24, thereby applying a flow force to the liquid inside. The pump 74 may be disposed so as to be in contact with a portion of the sensor flow path 46 between the second connection portion 40 and the first sensor 26 in a set state. The pump 74 performs first rotation operation (e.g., rotation operation in a direction of an arrow R1) such that a flow force in a direction toward the first sensor 26 (e.g., waste liquid storage portion 22) is applied to the liquid circulating through the sensor flow path 46. The pump 74 may perform second rotational operation (e.g., rotational operation in a direction of an arrow R2) such that a flow force in the direction toward the second connection portion 40 is applied to the liquid circulating through the sensor flow path 46.

The controller 16 (i.e., control unit) may include a computer having a processor, a memory, and an input/output interface (not illustrated). The controller 16 performs overall control of the entire system by the processor executing a program stored in the memory. The controller 16 is connected to the circuit control device 14 by communication means including wired, wireless, network, or a combination thereof. Specifically, the controller 16 controls operation of the plurality of clamps 72 and the pump 74.

Next, a sampling method using the sampling system 10 will be described.

Figure 3:
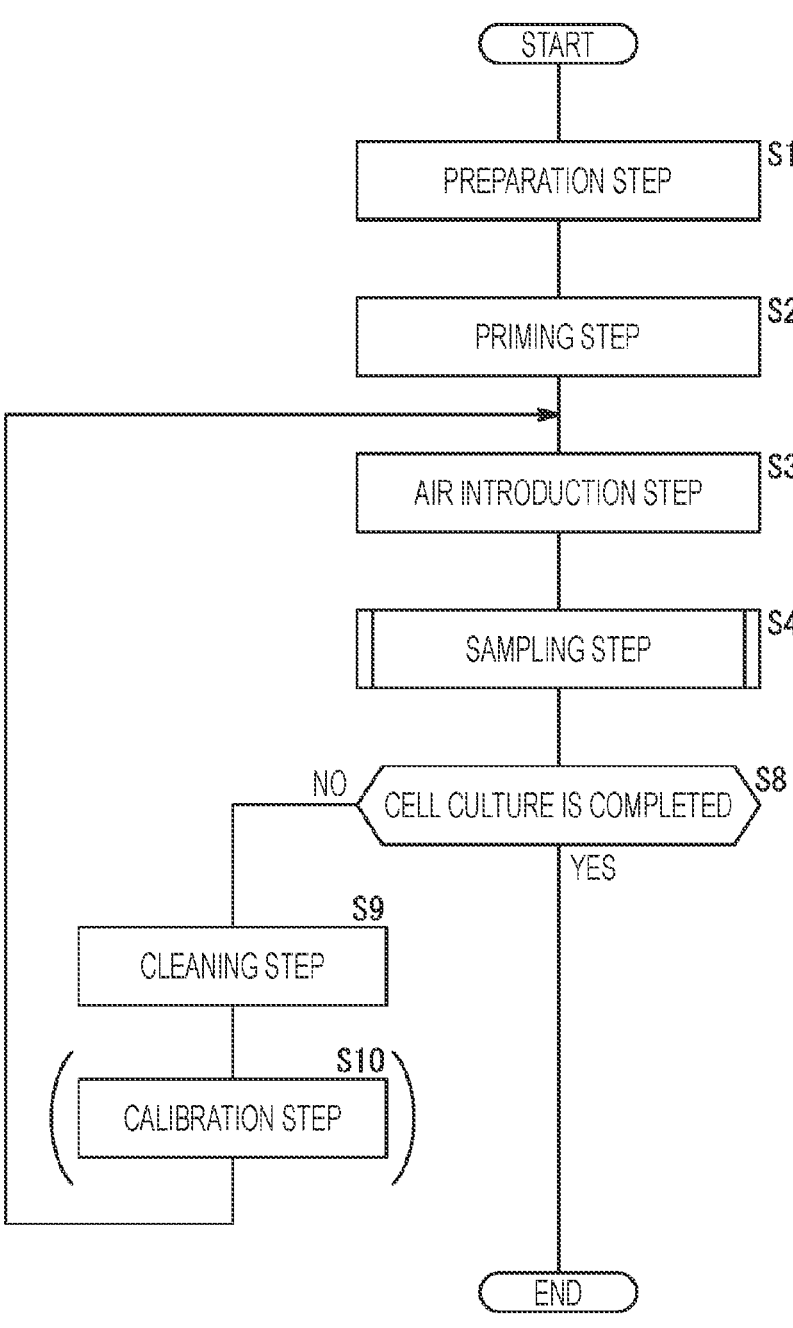
FIG. 3 is a flowchart illustrating a sampling method for using the sampling system illustrated in FIG. 1.

As illustrated in FIG. 3, the sampling method may include a preparation step, a priming step, an air introduction step, a sampling step, a cleaning step, and/or a calibration step.

First, in the preparation step (step S1), as illustrated in FIGS. 1 and 2, the sampling kit 12 may be attached (e.g., set) to the circuit control device 14, the introduction connector 42 of the first sample introduction path 34a may be connected to the sampling connector 228 of the first cell culture device 200A, and the introduction connector 42 of the second sample introduction path 34b may be connected to the sampling connector 228 of the second cell culture device 200B.

Figure 5:
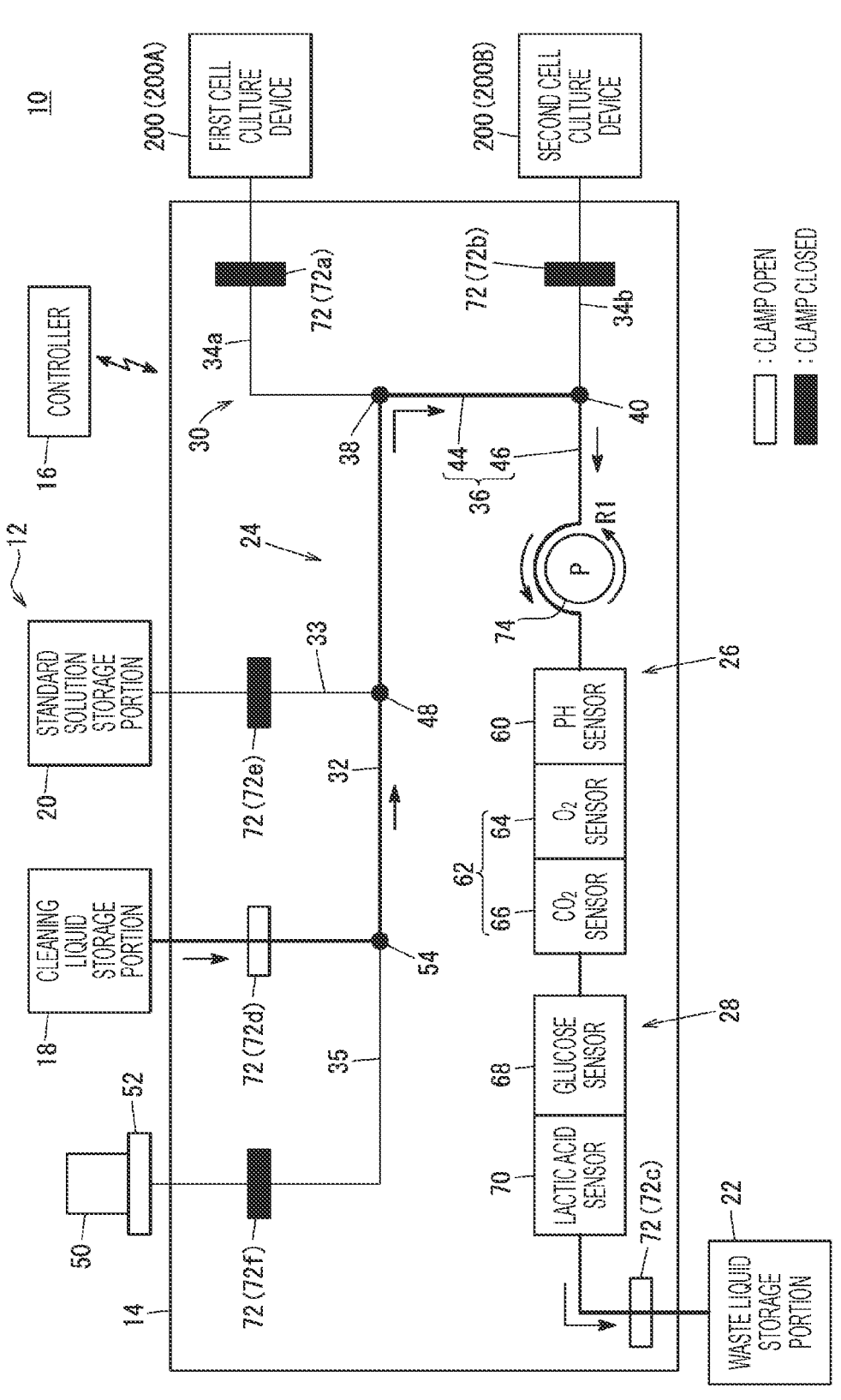
FIG. 5 is a schematic illustrating a first operation of the sampling method illustrated in FIGS. 3 and 4.

Subsequently, in the priming step (step S2 in FIG. 3), as illustrated in FIG. 5, the controller 16 may be configured to cause the pump 74 to perform the first rotation operation in a state where the third clamp 72c and the fourth clamp 72d are opened and the first clamp 72a, the second clamp 72b, the fifth clamp 72e, and the sixth clamp 72f are closed. Then, the cleaning liquid in the cleaning liquid storage portion 18 may be guided from the introduction path 32 to the waste liquid storage portion 22 via the first connection portion 38, the intermediate flow path 44, the second connection portion 40, and the sensor flow path 46 by the action of the pump 74.

Figure 6:
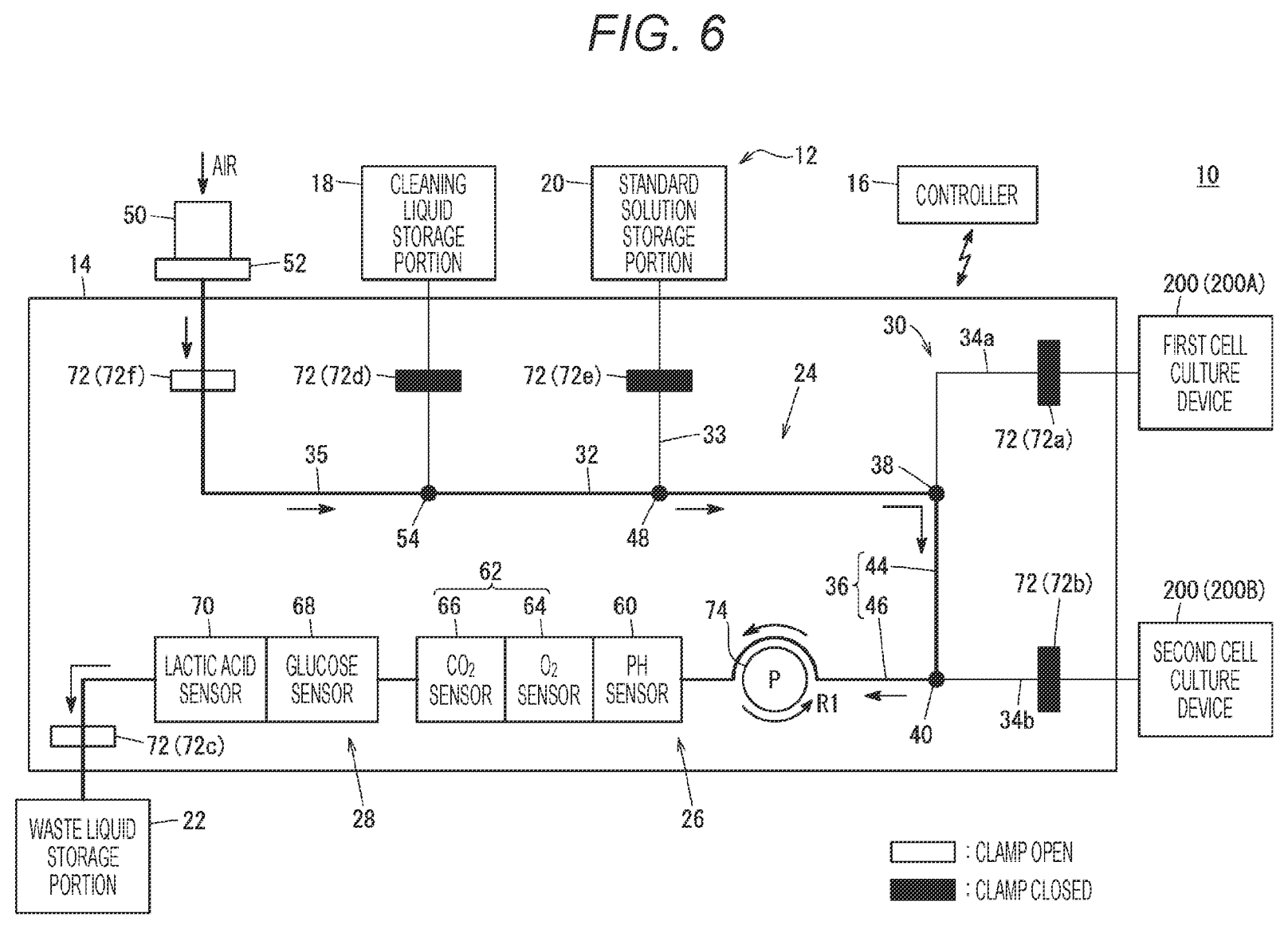

Thereafter, the air introduction step (step S3 in FIG. 3) is performed. Specifically, as illustrated in FIG. 6, the controller 16 may be configured to cause the pump 74 to perform the first rotation operation in a state where the third clamp 72c and the sixth clamp 72f are opened and the first clamp 72a, the second clamp 72b, the fourth clamp 72d, and the fifth clamp 72e are closed. Then, the air introduced from the air port portion 50 to the air introduction path 35 via the sterile filter 52 may be guided to the waste liquid storage portion 22 via the introduction path 32, the first connection portion 38, the intermediate flow path 44, the second connection portion 40, and the sensor flow path 46. As a result, the cleaning liquid remaining in the portion between the fourth connection portion 54 and the first connection portion 38 in the introduction path 32, the intermediate flow path 44, the sensor flow path 46, the first sensor 26, and the second sensor 28 may be pushed out to the waste liquid storage portion 22.

The air introduction step is not limited to an example where the air introduced into the air introduction path 35 may be guided to the waste liquid storage portion 22. In the air introduction step, it is sufficient that the air introduced into the air introduction path 35 can be guided to at least the first connection portion 38. In other words, a timing of stopping introduction of air (e.g., stopping driving of the pump) in the air introduction step may be a time point at which air may be guided to the intermediate flow path 44, a time point at which air may be guided to a portion between the second connection portion 40 and the first sensor 26 in the sensor flow path 46, a time point at which air may be guided between the first sensor 26 and the second sensor 28 in the sensor flow path 46, or the like.

Then, the sampling step (step S4 in FIG. 3) may be performed. Specifically, the controller 16 may be configured to select a sample to be collected (step S5 in FIG. 4). In other words, the controller 16 may be configured to select which one of the sample (e.g., first sample) of the first cell culture device 200A and the sample (e.g., second sample) of the second cell culture device 200B is to be collected on the basis of a cell culture state of the cell culture device 200.

Figure 4:
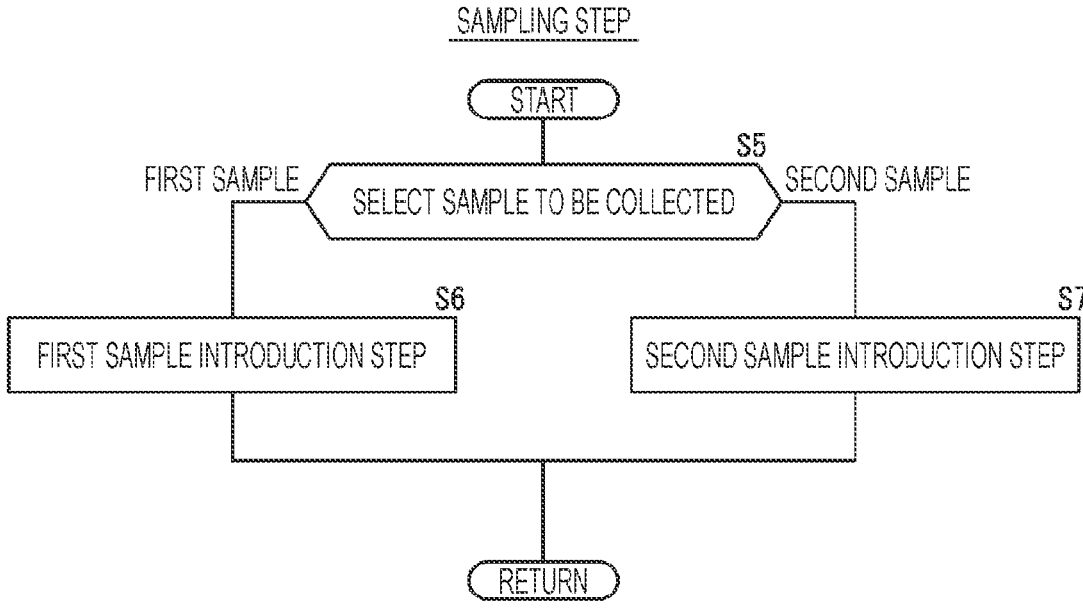
FIG. 4 is a flowchart further illustrating the sampling step as illustrated in FIG. 3.
Figure 7:
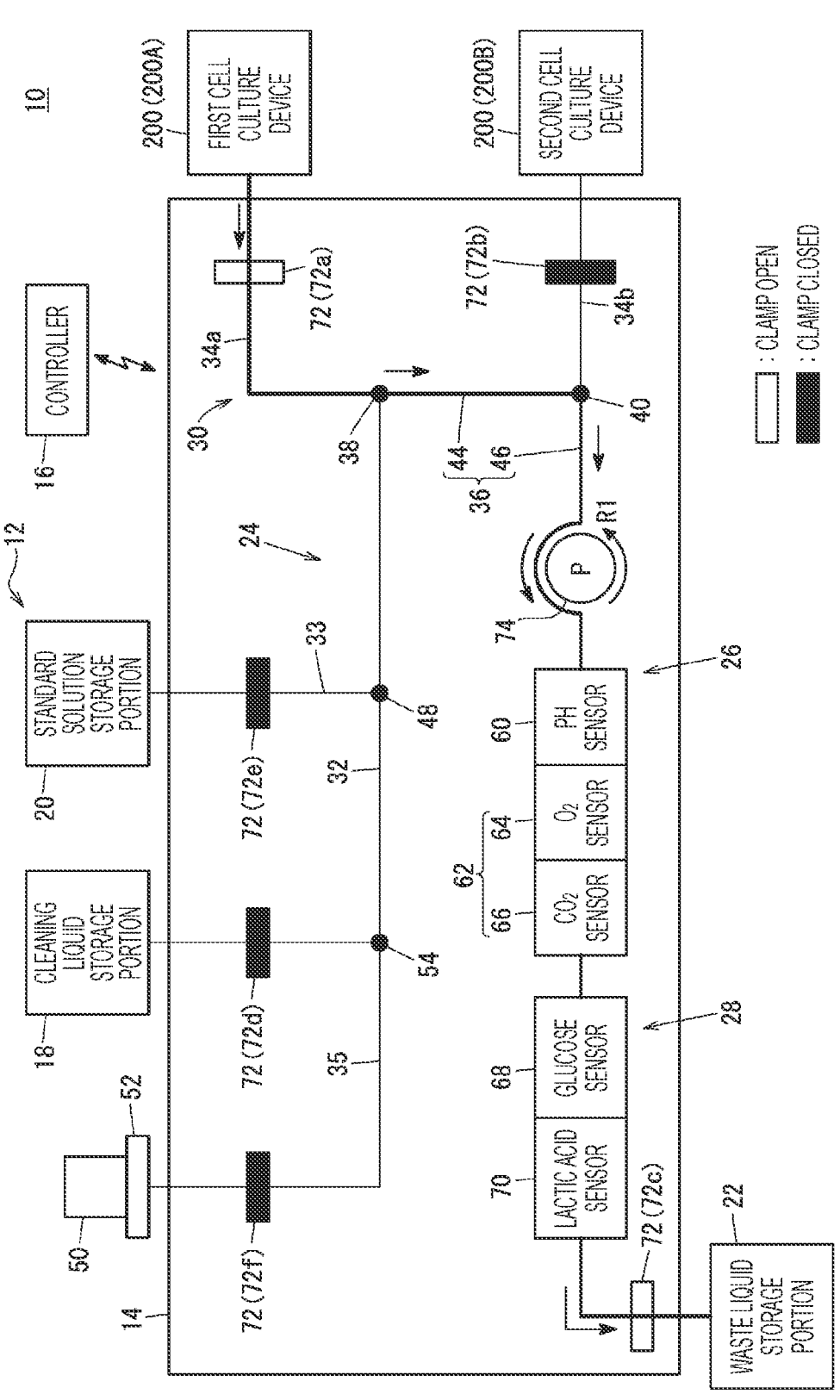
FIG. 7 is a schematic illustrating a third operation of the sampling method illustrated in FIGS. 3 and 4.

In a case where the controller 16 selects to collect the first sample, the first sample introduction step may be performed (step S6 in FIG. 4). In other words, as illustrated in FIG. 7, the controller 16 causes the pump 74 to perform the first rotation operation in a state where the first clamp 72a and the third clamp 72c are opened and the second clamp 72b, the fourth clamp 72d, the fifth clamp 72e, and the sixth clamp 72f are closed. Then, the first sample of the first cell culture device 200A may be guided to the waste liquid storage portion 22 via the first sample introduction path 34a, the first connection portion 38, the intermediate flow path 44, the second connection portion 40, and the sensor flow path 46 by the action of the pump 74.

In this event, the cleaning liquid does not remain in the vicinity of the first connection portion 38 in the introduction path 32 (e.g., the cleaning liquid is replaced with air in the air introduction step), and thus, the cleaning liquid is not mixed into the first sample circulating in the sampling channel 30.

The first sensor 26 and/or the second sensor 28 may be in contact with the first sample. In the first sensor 26, the pH, the $O_2$ concentration, and/or the $CO_2$ concentration in the first sample may be measured. The measurement results of the first sensor 26 may be transmitted to the controller 16. In the second sensor 28, the glucose concentration and/or the lactic acid concentration in the first sample may be measured. The measurement results of the second sensor 28 may be transmitted to the controller 16. The controller 16 may be configured to control culture conditions of the first cell culture device 200A on the basis of the measurement results of the first sensor 26 and the second sensor 28.

Figure 8:
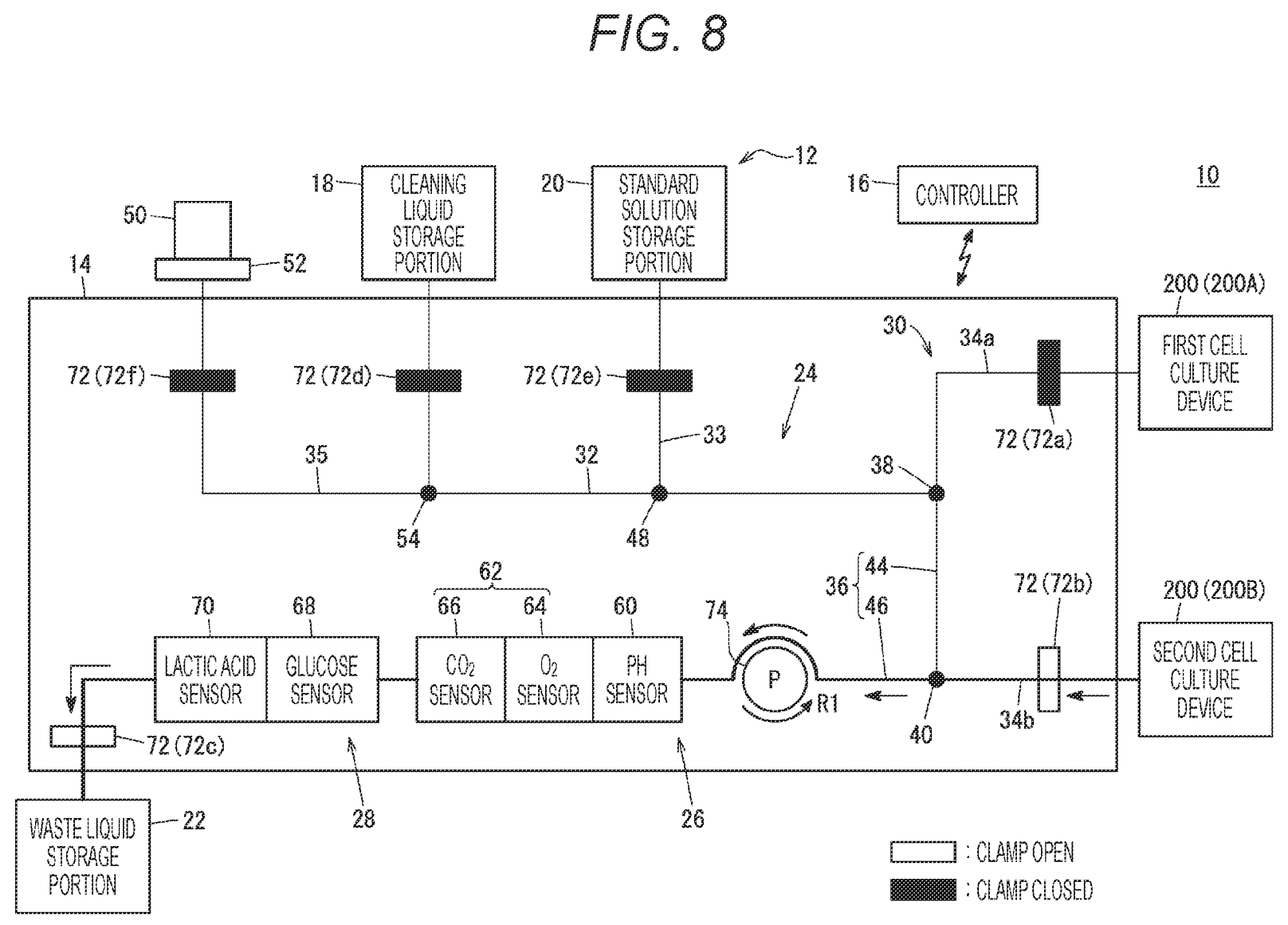

In a case where the controller 16 selects to collect the second sample, the second sample introduction step may be performed (step S7 in FIG. 4). In other words, as illustrated in FIG. 8, the controller 16 may be configured to cause the pump 74 to perform the first rotation operation in a state where the second clamp 72b and the third clamp 72c are opened and the first clamp 72a, the fourth clamp 72d, the fifth clamp 72e, and the sixth clamp 72f are closed. Then, the second sample of the second cell culture device 200B may be guided to the waste liquid storage portion 22 via the second sample introduction path 34b, the second connection portion 40, and the sensor flow path 46 by the action of the pump 74.

In this event, the cleaning liquid does not remain in the intermediate flow path 44 (e.g., the cleaning liquid is replaced with air in the air introduction step), and thus, the cleaning liquid is not mixed into the second sample circulating in the sampling channel 30.

The first sensor 26 and/or the second sensor 28 may be in contact with the second sample. In the first sensor 26, the pH, the $O_2$ concentration, and/or the $CO_2$ concentration in the second sample may be measured. The measurement results of the first sensor 26 may be transmitted to the controller 16. In the second sensor 28, the glucose concentration and/or the lactic acid concentration in the second sample may be measured. The measurement results of the second sensor 28 may be transmitted to the controller 16. The controller 16 may be configured to control culture conditions of the second cell culture device 200B on the basis of the measurement results of the first sensor 26 and the second sensor 28.

Upon completion of the sampling step, the controller 16 in FIG. 3 may be configured to determine whether or not the cell culture of the first cell culture device 200A and the second cell culture device 200B has been completed (step S8). In a case where the controller 16 determines that the cell culture has not been completed (step S8: NO), the cleaning step (step S9) may be performed. In the cleaning step, as illustrated in FIG. 5, the controller 16 may be configured to operate the plurality of clamps 72 and the pump 74 similarly to the priming step. Then, the cleaning liquid in the cleaning liquid storage portion 18 may circulate in the first sensor 26 and/or the second sensor 28 and may be guided to the waste liquid storage portion 22.

As a result, in the first sensor 26, the sample attached to each of the pH sensor 60, the $O_2$ sensor 64, and/or the $CO_2$ sensor 66 may be removed by the cleaning liquid. In the second sensor 28, the sample attached to each of the glucose sensor 68 and/or the lactic acid sensor 70 may be removed by the cleaning liquid.

Figure 9:
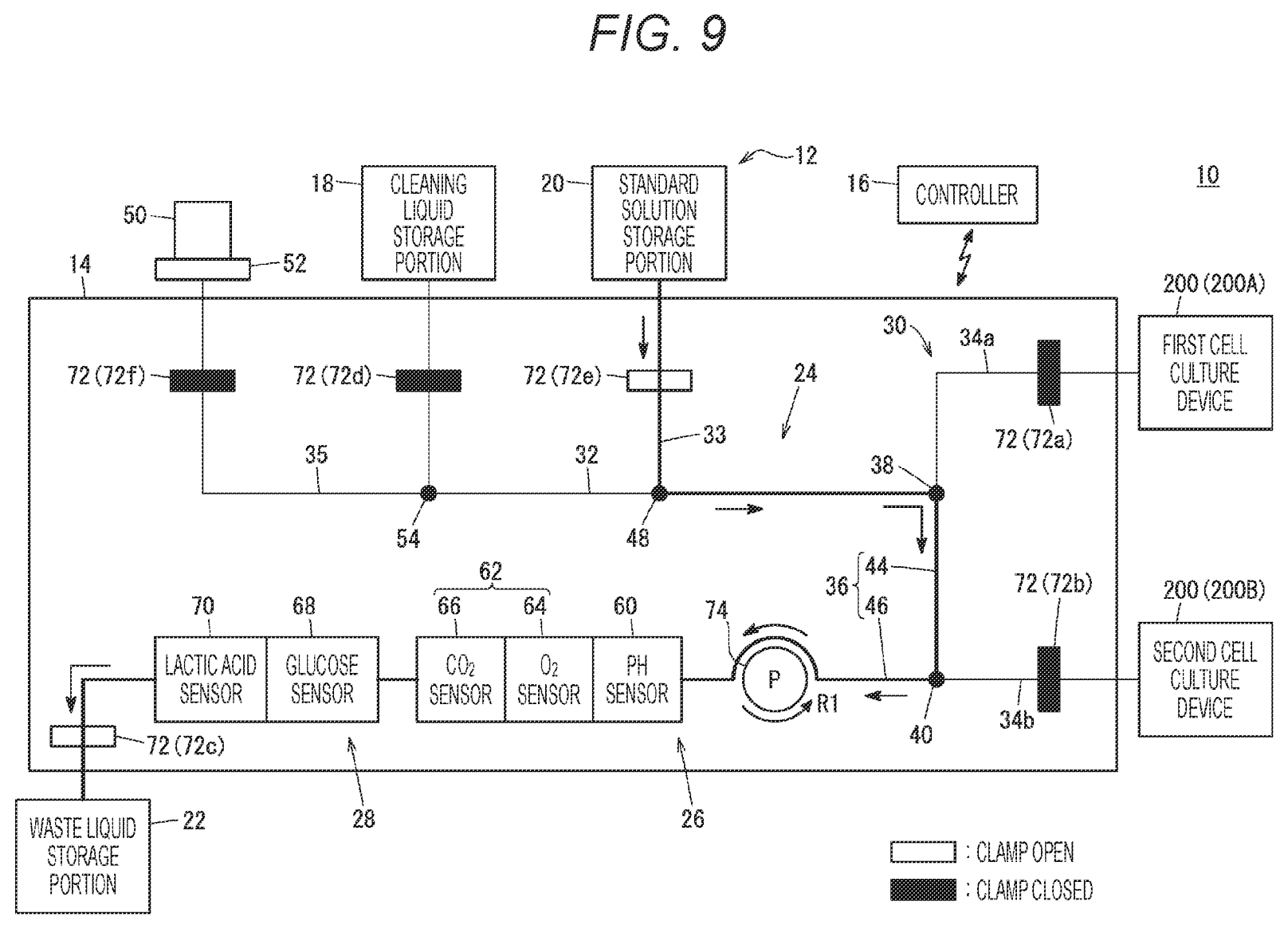

Thereafter, the calibration step (step S10 in FIG. 3) may be performed as necessary. In the calibration step, as illustrated in FIG. 9, the controller 16 may be configured to open the third clamp 72c and the fifth clamp 72e and to cause the pump 74 to perform the first rotation operation in a state where the first clamp 72a, the second clamp 72b, the fourth clamp 72d, and the sixth clamp 72f are closed. Then, the standard solution in the standard solution storage portion 20 may be guided to the waste liquid storage portion 22 via the standard solution introduction path 33, the introduction path 32, the first connection portion 38, the intermediate flow path 44, the second connection portion 40, and the sensor flow path 46 by the action of the pump 74.

In this event, the first sensor 26 may be configured to measure the pH, the $O_2$ concentration, and/or the $CO_2$ concentration in the standard solution. The measurement results of the first sensor 26 may be transmitted to the controller 16. The controller 16 may calibrate the pH sensor 60, the $O_2$ sensor 64, and/or the $CO_2$ sensor 66 on the basis of the measurement results of the first sensor 26. The second sensor 28 may be configured to measure the glucose concentration and/or the lactic acid concentration in the standard solution. The measurement results of the second sensor 28 may be transmitted to the controller 16. The controller 16 may calibrate the glucose sensor 68 and/or the lactic acid sensor 70 on the basis of the measurement results of the second sensor 28. When the calibration step is completed, the steps after step S3 are sequentially performed. In the present embodiment, the sampling step may be performed two or more times.

In a case where it is determined by the controller 16 that the cell culture has been completed (step S8 in FIG. 3: YES), a series of operation flow ends.

In at least one example embodiment, after circulating the first sample from the first cell culture device 200A to the sampling channel 30 and measuring the concentrations of the predetermined components in the first sample by the second sensor 28, the cleaning liquid may be circulated from the introduction path 32 to the second sensor 28 via the sampling channel 30. Thus, the sample attached to the second sensor 28 in the sampling step can be removed in the cleaning step. After the cleaning step, air may be introduced from the introduction path 32 into the sampling channel 30, so that the cleaning liquid remaining in the vicinity of the first connection portion 38 in the introduction path 32 can be pushed out to the sampling channel 30 by the air. It is therefore possible to prevent the cleaning liquid from being mixed into the sample during the sampling step.

The sampling system 10 may include the first clamp 72a that is configured to open and close the upstream side of the first connection portion 38 in the sampling channel 30, the fourth clamp 72d that is configured to open and close the introduction path 32, the pump 74 provided downstream of the first connection portion 38 in the sampling channel 30, the air introduction path 35 that is connected downstream of the fourth clamp 72d in the introduction path 32 and is opened to the atmosphere, and the sixth clamp 72f that is configured to open and close the air introduction path 35. In the air introduction step, air may be guided from the air introduction path 35 to the sampling channel 30 via the introduction path 32 by driving the pump 74 in a state where the first clamp 72a and the fourth clamp 72d are closed and the sixth clamp 72f is opened.

According to such a method, air can be introduced from the air introduction path 35 to the sampling channel 30 via the introduction path 32 with a simple configuration and control.

The air introduction path 35 is provided with the sterile filter 52. In the air introduction step, the air that has passed through the sterile filter 52 may be guided to the sampling channel 30.

According to such a method, the sample can be held in a sterile state by the sterile filter 52.

The gas concentration sensor 62 measures a gas concentration in the sample and is provided downstream of the first connection portion 38 in the sampling channel 30. In the air introduction step, air is introduced until the sample remaining in the gas concentration sensor 62 is replaced with air.

According to such a method, it may be possible to prevent the cleaning liquid remaining inside the gas concentration sensor 62 from being mixed into the sample.

The sampling channel 30 includes the sample flow path 36 provided with the second sensor 28 and forming a downstream side of the first connection portion 38 with the introduction path 32 in the sampling channel 30, the first sample introduction path 34a that guides the first sample of the first cell culture device 200A to the first connection portion 38, and the second sample introduction path 34b that guides the second sample of the second cell culture device 200B to the upstream side of the second sensor 28 in the sample flow path 36. The sampling step includes a first sample introduction step of introducing the first sample of the first cell culture device 200A from the first sample introduction path 34a into the sample flow path 36, and a second sample introduction step of introducing the second sample of the second cell culture device 200B from the second sample introduction path 34b into the sample flow path 36. In the air introduction step, the air may be guided to the downstream side of the second connection portion 40 with the second sample introduction path 34b in the sample flow path 36.

According to such a method, it may be possible to prevent the cleaning liquid from being mixed into the second sample when the second sample introduction step is performed.

The sampling system 10 may collect a sample of one cell culture device 200 and measure concentrations of predetermined components. In this case, the sampling system 10 does not have to include the second sample introduction path 34b. In addition, the sampling system 10 may collect samples of three or more cell culture devices 200 individually and measure concentrations of predetermined components. In other words, the number of cell culture devices 200 connected to the sampling channel 30 may be three or more. In such instances, sample introduction paths of the number corresponding to the number of cell culture devices 200 can be provided. The air introduction path 35 may be connected to a portion between the first connection portion 38 and the third connection portion 48 in the introduction path 32.

The present disclosure is not limited to the embodiment described above and may be modified in various manners without departing from the gist of the present disclosure. In the example embodiments described above, the cell culture system in which the sampling system 10 and the cell culture device 200 are configured separately is illustrated, but it should be appreciated that in other example embodiments, the cell culture system may be one in which the sampling system 10 and the cell culture device 200 are integrated.

In at least one example embodiment, a sampling system (10) includes a sampling channel (30) that collects a liquid sample of a cell culture device (200), a biosensor (28) that is provided in the sampling channel so as to be in contact with the sample and is configured to measure concentrations of predetermined components in the sample, an introduction path (32) that introduces a cleaning liquid to an upstream side of the biosensor in the sampling channel, and an air introduction path (35) that is connected to the introduction path and opened to an atmosphere, in which air introduced from the air introduction path can flow into the sampling channel through the introduction path.

In at least one example embodiment, a gas concentration sensor (62) that is configured to measure a gas concentration in the sample may be provided downstream of a connection portion (38) between the sampling channel and the introduction path.

In at least one example embodiment, the sampling channel may include: a sample flow path (36) provided with the biosensor and forming a downstream side of a connection portion with the introduction path in the sampling channel; a first sample introduction path (34a) that guides a first sample of a first cell culture device (200A) that is the cell culture device to the connection portion; and a second sample introduction path (34b) that guides a second sample of a second cell culture device (200B) to an upstream side of the biosensor in the sample flow path.

In at least one example embodiment, a sampling method may use a sampling system that includes a sampling channel that collects a liquid sample of a cell culture device, a biosensor provided in the sampling channel so as to be in contact with the sample, and an introduction path that introduces a cleaning liquid to an upstream side of the biosensor in the sampling channel. The sampling method may include a sampling step of circulating the sample from the cell culture device to the sampling channel and measuring concentrations of predetermined components in the sample by the biosensor; a cleaning step of circulating the cleaning liquid from the introduction path to the biosensor via the sampling channel after the sampling step; and an air introduction step of introducing air from the introduction path to the sampling channel, in which the sampling step is performed two or more times, and the second and subsequent sampling steps are performed after the air introduction step.

In at least one example embodiment, the sampling system may include a first opening/closing portion (72a) that is configured to open and close an upstream side of a connection portion of the sampling channel with the introduction path; a second opening/closing portion (72d) that is configured to open and close the introduction path; a pump (74) that is provided on a downstream side of the connection portion in the sampling channel; an air introduction path that is connected to a downstream side of the second opening/ closing portion in the introduction path and is opened to an atmosphere; and a third opening/closing portion (72f) that is configured to open and close the air introduction path, and in the air introduction step, the air may be guided from the air introduction path to the sampling channel via the introduction path by driving the pump in a state where the first opening/closing portion and the second opening/closing portion are closed and the third opening/closing portion is opened.

In at least one example embodiment, a sterile filter (52) may be provided in the air introduction path, and in the air introduction step, the air that passes through the sterile filter may be guided to the sampling channel.

In at least one example embodiment, a gas concentration sensor that measures a gas concentration in the sample may be provided on a downstream side of a connection portion with the introduction path in the sampling channel, and in the air introduction step, the air may be introduced until the sample remaining in the gas concentration sensor is replaced with the air.

In at least one example embodiment, the sampling channel may include a sample flow path provided with the biosensor and forming a downstream side of a connection portion with the introduction path in the sampling channel, a first sample introduction path that guides a first sample of a first cell culture device that is the cell culture device to the connection portion, and a second sample introduction path that guides a second sample of a second cell culture device to an upstream side of the biosensor in the sample flow path, the sampling step may include a first sample introduction step of introducing the first sample of the first cell culture device from the first sample introduction path into the sample flow path, and a second sample introduction step of introducing the second sample of the second cell culture device from the second sample introduction path into the sample flow path, and in the air introduction step, the air may be guided to the downstream side of a connection portion (40) with the second sample introduction path in the sample flow path.

The invention claimed is:

1. A sampling system comprising:
   a sampling channel system configured to receive a liquid sample from a cell culture device;
   a biosensor disposed in the sampling channel system so as to be in fluid communication with the liquid sample and configured to measure concentrations of predetermined components in the liquid sample;

an introduction path that is configured to introduce a cleaning liquid to the sampling channel system upstream of the biosensor, the cleaning liquid including a buffer solution or physiological saline; and
   an air path connected to the introduction path and opened to an atmosphere, wherein air guided from the air path flows into the sampling channel system through the introduction path.

2. The sampling system of claim 1, wherein the introduction path is coupled to the sampling channel system upstream of the biosensor.

3. The sampling system of claim 2, wherein a gas concentration sensor configured to measure a gas concentration in the liquid sample is provided in the sampling channel system downstream of a connection portion coupling the sampling channel system and the introduction path and upstream of the biosensor.

4. The sampling system of claim 3, wherein a pH sensor configured to measure the pH in the liquid sample is provided in the sampling channel system downstream of the connection portion coupling the sampling channel system and the introduction path and upstream of the biosensor.

5. The sampling system of claim 1, wherein
   the sampling channel system includes a sample flow path downstream of a connection portion coupling the sampling channel system and the introduction path,
   the liquid sample is a first liquid sample and the cell culture device is a first cell culture device, and
   the sampling system includes a first sample introduction path that guides the first liquid sample to the connection portion.

6. The sampling system of claim 5, wherein the sampling channel system further includes a second sample introduction path that guides a second liquid sample from a second cell culture device to the sample flow path upstream of the biosensor.

7. The sampling system of claim 1, wherein the biosensor includes a glucose sensor configured to measure a glucose concentration in the liquid sample, a lactic acid sensor configured to measure a lactic acid concentration in the liquid sample, or a combination of a glucose sensor configured to measure a glucose concentration in the liquid sample and a lactic acid sensor configured to measure a lactic acid concentration in the liquid sample.

8. The sampling system of claim 1, wherein the air path includes an air port portion opened to the atmosphere and a sterile filter disposed within the air port portion and configured to maintain a sterile state of the sampling system.

9. The sampling system of claim 1, wherein the sampling system further includes:
   a first clamp configured to open and close the sampling channel system upstream of a connection portion coupling the sampling channel system and the introduction path upstream of the biosensor;
   a second clamp configured to open and close the introduction path;
   a pump provided in the sampling channel system downstream of the connection portion and upstream of the biosensor;
   the air path connected to the introduction path upstream of the second clamp; and
   a third clamp that opens and closes the air path.

10. The sampling system of claim 1, wherein the introduction path is also configured to introduce a standard solution selected for calibrating the biosensor.

11. A sampling method comprising:

a sampling step including moving a liquid sample disposed in a sampling channel system of a sampling system and received from cell culture device, the sampling system including a biosensor disposed in the sampling channel system and in fluid contact with the sample, and measuring concentrations of predetermined components in the sample by the biosensor;

a cleaning step including introducing a cleaning liquid from an introduction path of the sampling system to sampling channel system upstream of the biosensor, the cleaning liquid including a buffer solution or physiological saline, and moving the cleaning liquid through the sampling channel system; and an air introduction step including introducing air from the introduction path to the sampling channel system, wherein the sampling step is performed two or more times, and a second and subsequent sampling steps are performed after the air introduction step.

12. The sampling method of claim 11, wherein the sampling system further includes:

a first clamp configured to open and close the sampling channel system upstream of a connection portion coupling the sampling channel system and the introduction path upstream of the biosensor;

a second clamp configured to open and close the introduction path;

a pump provided in the sampling channel system downstream of the connection portion and upstream of the biosensor;

an air path connected to the introduction path upstream of the second clamp; and a third clamp that opens and closes the air path, and in the air introduction step, the air is guided from the air path to the sampling channel system via the introduction path by driving the pump in a state where the first clamp and the second clamp are closed and the third clamp is opened.

13. The sampling method of claim 12, wherein the air path is provided with a sterile filter, and in the air introduction step, the air that has passed through the sterile filter is guided to the sampling channel system.

14. The sampling method of claim 12, wherein a gas concentration sensor that measures a gas concentration in the liquid sample is provided on a downstream side of a connection portion coupling sampling channel system and the introduction path and upstream of the biosensor.

15. The sampling method of claim 14, wherein in the air introduction step, the air is introduced until the sample remaining in the gas concentration sensor is replaced with the air.

16. The sampling method of claim 11, wherein the sampling channel system includes a sample flow path downstream of a connection portion coupling the sampling channel system and the introduction path, the liquid sample is a first liquid sample and the cell culture device is a first cell culture device, the sampling system includes a first sample introduction path that guides the first liquid sample to a connection portion coupling the sampling channel system and the introduction path upstream of the biosensor, and the sampling step includes a first sample introduction step of introducing the first liquid sample into the sample flow path.

17. The sampling method of claim 16, wherein the sampling channel system further includes a second sample introduction path that guides a second liquid from a second cell culture device to the sample flow path upstream of the biosensor; and the sampling step further includes a second sample introduction step of introducing the second liquid into the sample flow path.

18. A sampling system comprising:

a sampling channel system configured to receive a liquid sample from a cell culture device and including a sensor for communicating with the liquid sample and configured to measure concentrations of components in the liquid sample; and an introduction path configured to introduce a cleaning liquid to the sampling channel system upstream of the sensor and also configured to introduce a standard solution selected for calibrating the sensor upstream of the sensor, the introduction path including an air path that includes an air port portion opened to the atmosphere and having a sterile filter disposed therewithin the that is configured to maintain a sterile state of the sampling system.

19. The sampling system of claim 18, wherein the sensor is a first sensor and the first sensor includes a biosensor, and the sampling system further includes a second sensor downstream of a connection portion coupling the sampling channel system and the introduction path and upstream of the first sensor, the second sensor including a gas sensor configured to measure a gas concentration in the liquid sample.

\*    \*    \*    \*    \*